United States Patent
Ten Kate et al.

(10) Patent No.: US 11,236,039 B2
(45) Date of Patent: *Feb. 1, 2022

(54) MULTI-STEP PROCESS FOR CONVERTING CYCLIC ALKYLENEUREAS INTO THEIR CORRESPONDING ALKYLENEAMINES

(71) Applicant: NOURYON CHEMICALS INTERNATIONAL B.V., Arnhem (NL)

(72) Inventors: Antoon Jacob Berend Ten Kate, Arnhem (NL); Michiel Jozef Thomas Raaijmakers, Deventer (NL); Karl Fredrik Lake, Södertälje (SE); Eike Nicolas Kantzer, Uddevalla (SE); Slavisa Jovic, Utrecht (NL); Rolf Krister Edvinsson, Partille (SE); Ina Ehlers, Stenungsund (SE); Hendrik Van Dam, Ede (NL); Rens Veneman, Amersfoort (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/638,389

(22) PCT Filed: Aug. 7, 2018

(86) PCT No.: PCT/EP2018/071319
§ 371 (c)(1),
(2) Date: Feb. 11, 2020

(87) PCT Pub. No.: WO2019/030190
PCT Pub. Date: Feb. 14, 2019

(65) Prior Publication Data
US 2020/0165187 A1 May 28, 2020

(30) Foreign Application Priority Data
Aug. 11, 2017 (EP) .................................... 17185945

(51) Int. Cl.
*C07C 209/62* (2006.01)
*B01D 3/00* (2006.01)
*C07C 209/86* (2006.01)
*C07C 213/00* (2006.01)

(52) U.S. Cl.
CPC .......... *C07C 209/62* (2013.01); *C07C 209/86* (2013.01); *C07C 213/00* (2013.01)

(58) Field of Classification Search
CPC ............................. C07C 209/62; B01D 3/009
See application file for complete search history.

(56) References Cited

U.S. PATENT DOCUMENTS

| | | | | |
|---|---|---|---|---|
| 2,812,333 A * | 11/1957 | Steele | .................. | C07D 233/32 548/323.5 |
| 4,387,249 A | 6/1983 | Harnden et al. | | |
| 4,503,250 A | 3/1985 | Herdle | | |
| 5,994,585 A | 11/1999 | Günther-Hanssen | | |
| 10,428,010 B2 * | 10/2019 | Edvinsson | ........... | C07D 233/36 |
| 2008/0045738 A1 | 2/2008 | Orschel et al. | | |
| 2020/0223785 A1 * | 7/2020 | Raaijmakers | ......... | C07C 209/62 |

FOREIGN PATENT DOCUMENTS

JP      2007527895 A    10/2007
RU      2215734 C2      11/2003

OTHER PUBLICATIONS

EPO, European Extended Search Report issued in European Application No. 17185945.7.
EPO, International Search Report and Written Opinion issued in International Application No.

* cited by examiner

*Primary Examiner* — Yong L Chu
(74) *Attorney, Agent, or Firm* — Lorenz & Kopf, LLP (57) ABSTRACT

The invention pertains to a process for converting a feedstock comprising cyclic alkyleneureas into their corresponding alkyleneamines, comprising —a $CO_2$ removal step in which cyclic alkyleneureas are converted into their corresponding alkyleneamines by reacting cyclic alkyleneureas in the liquid phase with water with removal of $CO_2$, —an amine removal step wherein cyclic alkyleneureas are converted in a reactive separation process into their corresponding alkyleneamines by reaction with an amine compound selected from the group of primary amines or secondary amines which have a higher boiling point than the alkyleneamines formed during the process. It has been found that the combination of a $CO_2$ removal step and an amine removal step makes it possible to convert alkyleneureas into the corresponding amines in an efficient manner in a high reaction rate.

17 Claims, 2 Drawing Sheets

MULTI-STEP PROCESS FOR CONVERTING CYCLIC ALKYLENEUREAS INTO THEIR CORRESPONDING ALKYLENEAMINES

CROSS-REFERENCE TO RELATED APPLICATION

This application is a U.S. National-Stage entry under 35 U.S.C. § 371 based on International Application No. PCT/EP2018/071319, filed Aug. 7, 2018, which was published under PCT Article 21(2) and which claims priority to European Application No. 17185945.7, filed Aug. 11, 2017, which are all hereby incorporated in their entirety by reference.

TECHNICAL FIELD

The present invention pertains to a process for converting cyclic alkyleneureas into their corresponding alkyleneamines, in particular to a multi-step process.

BACKGROUND

Cyclic alkyleneureas are compounds comprising two nitrogen atoms connected by a carbonyl moiety and an alkylene moiety. For example, cyclic ethyleneurea is a compound comprising a cyclic ethyleneurea moiety in which two nitrogen atoms are connected by a carbonyl moiety and an ethylene moiety, in accordance with the following formula:

Cyclic alkyleneurea compounds can be converted into the corresponding alkyleneamines by removal of the CO group and addition of two hydrogen atoms. Alkyleneamines, in particular ethyleneamines, specifically in particular diethylene triamine (DETA) and higher ethyleneamines such as (linear) triethylene tetramine (L-TETA) and tetraethylenepentamine (L-TEPA) are attractive products from a commercial point of view. Cyclic ethyleneureas are therewith an attractive precursor in the manufacture of ethylenediamine and higher ethyleneamines.

It has been found, however, that cyclic alkyleneureas are relatively stable and difficult to convert to the corresponding alkyleneamines. This can also be seen from the prior art, where the conversion is carried out with large excesses of strong inorganic bases. The difficulty in converting cyclic alkyleneureas into the corresponding alkyleneamines using strong inorganic bases goes in particular for compounds where the alkyleneurea moiety is connected to further alkyleneamine moieties via the nitrogen atoms, in particular where the alkyleneurea moiety is present between two further alkyleneamine moieties.

U.S. Pat. No. 4,503,250 describes a process for preparing linear polyalkylene polyamines which comprises reacting ammonia or an alkyleneamine compound having two primary amino groups or mixtures thereof with an alcohol or an alkanolamine compound having a primary amino group and a primary or secondary hydroxyl group or mixtures thereof in the presence of a derivative of carbonic acid at a temperature at which the reaction will proceed under pressures sufficient to maintain the reaction mixture substantially in a liquid phase. The process results in the formation of urea adducts of polyalkylene polyamines. The urea adducts are converted to polyethylene polyamines by reaction with 50% aqueous KOH under reflux overnight. 8 moles KOH are used per mole carbon dioxide.

U.S. Pat. No. 4,387,249 discloses the reaction of ethylenediamine (EDA), ethanolamine (MEA) and urea to give aminoethylethyleneurea (UDETA) and ethyleneurea (EU), which are hydrolysed to form DETA and EDA. The hydrolysis step takes place in an inert atmosphere in the presence of a Brønsted base. The Brønsted base preferably is the hydroxide of an alkali metal, more preferably an aqueous solution of NaOH. In the examples hydrolysis takes place at a temperature of 200° C. under autogenous pressure, using a 5 mole/liter NaOH solution.

While quite effective, the process as described in these references has a number of disadvantages. The use of caustic bases has as a disadvantage that it results in low product selectivities due to degradation of the desired products. In addition, when using an (inorganic) base, salts are formed as by-products which complicate the following separation of organics, resulting in lower yields of the targeted product. In addition the combination of amines, water, salt and high temperatures can cause problems with corrosion, discolored products and decreased storage stability. Further, an outlet has to be found for processing the large amounts of salts.

U.S. Pat. No. 2,812,333 describes the hydrolysis of 1-(2-hydroxyethyl)imidazolinone-2 to the corresponding hydroxyethylethylenediamine by heating in the presence of water at elevated temperatures, with removal of CO2. The reaction takes place in a large excess of water; in the example a 12% solution of the 1-(2-hydroxyethyl)imidazolinone-2 is used. The conversion is low. Under test conditions approximately 5% of the compound hydrolysed per hour.

There is need in the art for a process for converting cyclic alkyleneureas into their corresponding alkyleneamines which combines a high conversion of cyclic alkyleneureas into the corresponding amines, while addressing the disadvantages of the prior art processes.

The present invention provides such a process.

The present invention provides a process for converting a feedstock comprising cyclic alkyleneureas into their corresponding alkyleneamines, comprising a CO2 removal step in which cyclic alkyleneureas are converted into their corresponding alkyleneamines by reacting cyclic alkyleneureas in the liquid phase with water with removal of CO2, an amine removal step wherein cyclic alkyleneureas are converted in a reactive separation process into their corresponding alkyleneamines by reaction with an amine compound selected from the group of primary amines or secondary amines which have a higher boiling point than the alkyleneamines formed during the process.

In general, in the CO2 removal step between 5% and 95% of alkyleneurea moieties present in the feedstock are converted into amine moieties, and in the amine removal step between 5% and 95% of alkyleneurea moieties present in the feedstock are converted into amine moieties.

It has been found that the combination of a CO2 removal step and an amine removal step makes it possible to convert alkyleneureas into the corresponding amines in an efficient manner in a high reaction rate. Further advantages of the present invention and specific embodiments thereof will become apparent from the further specification.

The invention will be discussed in more detail below.

BRIEF DESCRIPTION OF THE DRAWINGS

The present invention will hereinafter be described in conjunction with the following drawing figures, wherein like numerals denote like elements, and.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description.

The process according to the invention comprises two steps, namely a CO2 removal step and an amine removal step. In the CO2 removal step cyclic alkyleneureas are converted into their corresponding alkyleneamines by reacting cyclic alkyleneureas in the liquid phase with water, under removal of CO2. In the amine removal step cyclic alkyleneureas are converted in a reactive separation process into their corresponding alkyleneamines by reaction with an amine compound selected from the group of primary amines or secondary amines which have a higher boiling point than the alkyleneamines formed during the process, with removal of alkylene amine.

Accordingly, both steps convert cyclic alkyleneureas into the corresponding amines, but by two different mechanisms.

In the CO2 removal step, the alkyleneureas are hydrolysed in reaction with water, resulting in the formation of alkyleneamines and CO2, which is removed.

In the amine removal step, the alkyleneurea reacts with a primary or secondary amine to form an alkyleneamine and an alkyleneurea, with alkyleneamine being removed.

The two steps have different optima. This will be elucidated as follows:

In the conversion of urea adducts of alkyleneamine compounds into the corresponding amines by removal of CO2 it is relatively easy to convert the urea adducts at high adduct concentrations. When adduct concentrations decrease, it gets progressively more difficult to convert the urea adducts. Therefore, the CO2 removal step works best when the system comprises a relatively high amount of cyclic alkyleneureas and a relatively low amount of the corresponding amines.

This can be quantified via the CO2-loading of the system. The CO2-loading of the system can be defined as the amount of urea and carbamate moieties present in the system divided by the total of the amount of independent urea and carbamate moieties and —NH—CH2-CH2-NH— and —NH—CH2-CH2-OH moieties. In the above definition, it should be noted that e.g. compounds like diethylenetriamine (DETA) or aminoethanolethyleneamine (AEEA) only have one independent —NH—CH2-CH2-NH— or —NH—CH2-CH2-OH moiety as the middle amine can only be part of one moiety. The number of moieties —NH—CH2-CH2-NH— and —NH—CH2-CH2-OH are calculated assuming that all ureas and carbamates have been removed by hydrolysis. For example UDETA has the same number of —NH—CH2-CH2-NH— moieties as DETA.

Thus, the CO2-loading stands for the molar ratio between the number of urea and carbamate moieties present in the system and the total number of groups which can potentially form such adducts. The CO2-loading can be calculated from the composition of the system. It can, if so desired, also be determined via titration with a strong base.

It is preferred for the feed to the CO2 removal step to have a CO2-loading of at least 0.2, in particular at least 0.4, more in particular at least 0.6. The maximum preferably is 1.

On the other hand, the amine removal step works best at relatively low CO2-loading. In the amine removal step a CO moiety (in the urea group) is transferred from the urea-containing amine to be converted to an amine group of an amine with a higher boiling point. This works best if the number of amine groups in the system is relatively high. Therefore it is preferred for the feed to be provided to the amine removal step to have a CO2-loading of at most 0.8, more in particular at most 0.6. Because there has to be some urea adduct in the system to make it worthwhile to carry out the process, a value of 0.05 may be mentioned as a minimum value. The CO2-loading preferably is at least 0.1, in particular at least 0.2.

In the CO2 removal step, the CO2-loading of the system decreases, due to the removal of CO2 from the system. On the other hand, in the amine removal step the CO2-loading of the system increases, due to the removal of amine compounds from the system. Therefore, the sequence in which the two steps are performed may vary, depending on the CO2-loading of the composition to be treated.

In one embodiment, the present invention provides a process for converting a feedstock comprising cyclic alkyleneureas into their corresponding alkyleneamines, comprising the steps of providing a feedstock with a CO2-loading of at least 0.2 to a CO2 removal step in which cyclic alkyleneureas are converted into their corresponding alkyleneamines by reacting cyclic alkyleneureas in the liquid phase with water with removal of CO2, and providing at least part of the product of the CO2 removal step to an amine removal step wherein cyclic alkyleneureas are converted in a reactive separation process into their corresponding alkyleneamines by reaction with an amine compound selected from the group of primary amines or secondary amines which have a higher boiling point than the alkyleneamines formed during the process, with removal of alkyleneamine.

As will be evident to the skilled person, the product of the CO2 removal step which may be provided to the amine removal step is the reaction mixture from which CO2 has been removed.

The product of the amine removal step (that is, the product fraction from which amine has been removed) which has a higher CO2-loading than the feed to the amine removal step, can be provided to a further CO2 removal step or be recycled to the CO2 removal step, if this is desired. It can also be processed in other ways.

The product from the CO2 removal step can be provided directly to the amine removal step. However, intermediate steps may also be carried out. In particular, it may be attractive to subject the product from the CO2 removal step to a step wherein water and other light compounds are removed.

In another embodiment, the present invention provides a process for converting a feedstock comprising cyclic alkyleneureas into their corresponding alkyleneamines, comprising the steps of providing a feedstock with a CO2-loading of between 0.05 and 0.8 to an amine removal step wherein cyclic alkyleneureas are converted in a reactive separation process into their corresponding alkyleneamines by reaction with an amine compound selected from the group of primary amines or secondary amines which have a higher boiling point than the alkyleneamines formed during the process, with removal of alkyleneamines and providing at least part of the product of the amine removal step to a CO2 removal step in which cyclic alkyleneureas are converted into their corresponding alkyleneamines by reacting cyclic alkyleneureas in the liquid phase with water, with removal of CO2.

As will be evident to the skilled person, the product of the amine removal step which may be provided to the CO2 removal step is the fraction of the product from which amine has been removed.

As will be evident to the skilled person, the product of the CO2 removal step, which has a lower CO2-loading than the feed to the CO2 removal step, can be provided to a further amine removal step if this is desired. It can also be processed in other ways, depending on its composition.

The product from the amine removal step can be provided directly to the CO2 removal step. However, intermediate steps may also be carried out. In particular, it may be desirable to add water to the composition before it is provided to the CO2 removal step. This water can, e.g., be partially or in its entirety be a recycle stream from a water evaporation carried out between the CO2 removal step and the amine removal step, and/or from water recovered in the CO2 removal step, or water recovered in the amine removal step.

In general, when in the process according to the invention product from the CO2 removal step is provided to the amine removal step, it may be desired to provide part of the product from the CO2 removal step to the amine removal step, and remove another part in a purge. Conversely, when in the process according to the invention product from the amine removal step is provided to the CO2 removal step, it may be desired to provide part of the product from the amine removal step to the CO2 removal step, and remove another part in a purge.

As will be evident to the skilled person, when in the process according to the invention product from the CO2 removal step is provided to the amine removal step, it is possible to also provide other compositions containing cyclic alkyleneureas to the amine removal step, so that a combined composition is subjected to amine removal. Conversely, when in the process according to the invention product from the amine removal step is provided to the CO2 removal step, it is possible to also provide other compositions containing cyclic alkyleneureas to the CO2 removal step, so that a combined composition is subjected to CO2 removal.

The CO2 recovered from the CO2 removal step can be provided to other processes. Alkyleneamine recovered from the amine removal step can be the end product of the process. They can be subjected to further fractionation if so desired, with the different products being treated as desired.

Starting Compounds

The starting material used in the present invention is a reaction mixture comprising cyclic alkyleneureas. Cyclic alkyleneureas are compounds comprising two nitrogen atoms connected by a carbonyl moiety and an alkylene moiety. For example, in a cyclic ethyleneurea, two nitrogen atoms are connected through a carbonyl moiety and an ethylene moiety in accordance with the following formula:

In a preferred embodiment in the process of the invention the cyclic alkyleneurea that is subjected to the conversion to give a corresponding alkyleneamine are:

Wherein $R_1$ and $R_2$ each independently are chosen from the group of hydrogen, an alkyleneamine group of the formula $X-R_3-(NH-R_3-)_p-$, or an alkoxy group of formula $X-R_3-(O-R_3-)_n-$, or a group combining such alkyleneamine and alkoxy units p and n, wherein one or more units $\sim N-R_3-N\sim$ may be present as either one of the rings and wherein each $R_3$ independently is as defined below and X may be hydroxyl, amine, a linear or branched C1-C20 hydroxyalkyl or C1-C20 aminoalkyl group, n and p independently is at least 0, preferably 1-20, more preferably 2-20, optionally containing one or more piperazine, or alkyleneurea groups, or when p or n is 0 may be a C1-C20 hydroxyalkyl or C1-C20 aminoalkyl, and $R_3$ is alkylene or substituted alkylene.

In a preferred embodiment R2 is a hydrogen atom and R1 is not a hydrogen atom.

In a more preferred embodiment R2 is a hydrogen atom and R1 is a group that may contain a repeating alkyleneamine group, even more preferably a repeating ethyleneamine group of the formula $X-(NH-C_2H_4)_n$ wherein optionally one or more units $-NH-C_2H_4-NH-$ may be present as one of the rings and wherein n is 0 to 20, and X may be a hydrogen atom, an aminoalkyl, an hydroxyalkyl, N-imidazolidinonealkyl or piperazinoalkyl group, most preferably wherein the alkyl is ethyl.

R3 is preferably ethylene or propylene, optionally substituted with C1-C3 alkyl substituents. More preferably it is an unsubstituted ethylene, unsubstituted propylene or isopropylene, most preferably an unsubstituted ethylene.

Figure 1:
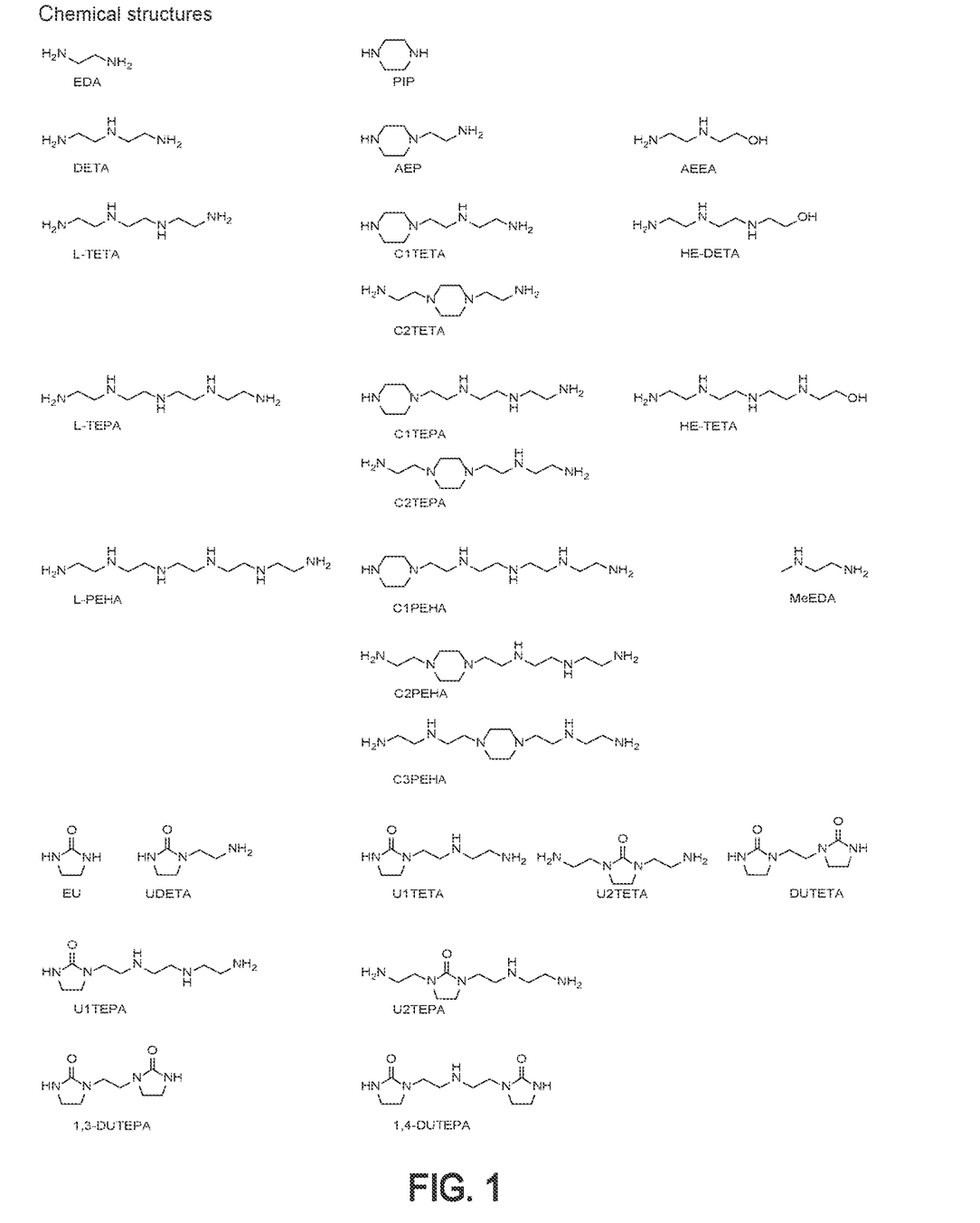
FIG. 1 illustrates the molecular structures of some cyclic alkyleneureas.

Some examples of cyclic alkylene ureas that are most preferred are EU (ethyleneurea), UDETA (the urea of diethylenetriamine), UTETA (the ureas of triethylenetetraamine, i.e. U1TETA or U2TETA, dependent on whether the urea is between the $1^{st}$ and $2^{nd}$ amine in the chain or $2^{nd}$ and $3^{rd}$ amine, respectively), DUTETA (the diurea of triethylenetetramine), UTEPA (the ureas of tetraethylenepentamine, i.e. U1TEPA, U2TEPA depending on where the urea unit is located), DUTEPA (DU1,3TEPA, DU1,4TEPA, the diureas of tetraethylenepentamine), UAEEA (the urea of aminoethylethanolamine), HE-UDETA (the urea of hydroxyethyl diethylenetriamine, that can exist in two isomers HE-U1DETA and HE-U2DETA), HE-UTETA (the urea of hydroxyethyl triethylenetetraamine, that can exist in three isomers HE-U1TETA, HE-U2TETA and HE-U3TETA), HE-DUTETA (the diurea of hydroxyethyl triethylenetetraamine), or any mixture of these. The molecular structures of a number of the above cyclic alkylene ureas are given in FIG. 1. To avoid any confusion, if a number is given for the amine group where the cyclic urea unit U is located, the amine groups are counted from the terminal amine group on the molecule which in the case of hydroxyethylated ethylene amines is the amine group at the end not containing the hydroxyl group.

The process according to the invention is particularly suitable for converting mixtures of alkyleneamines comprising at least 10 mole % of cyclic urea derivatives of alkyleneamine compounds comprising a —NH-R3-NH-R3-NH-R3-NH— moiety, calculated on the total of cyclic urea compounds present in the mixture. Cyclic urea derivatives of compounds having this moiety are relatively difficult to convert into the corresponding amines, and it is a feature of the process of the present invention that mixtures comprising these compounds can be converted while obtaining a high yield. It may be preferred for the starting material to be a mixture of alkyleneamines comprising at least 15 mole %, in particular at least 20 mole %, of cyclic urea derivatives of alkyleneamine compounds comprising a —NH-R3-NH-R3-NH-R3-NH— moiety, calculated on the total of cyclic urea compounds present in the mixture.

The CO2 Removal Step:

In the CO2 removal step cyclic alkyleneureas are converted into their corresponding alkyleneamines by reacting cyclic alkyleneureas in the liquid phase with water with removal of CO2.

The reaction with water generally takes place at a temperature of at least 150° C. If the reaction temperature is below 150° C., the cyclic alkyleneureas will not react to a significant extent. It is preferred for the reaction to be carried out at a temperature of at least 180° C., in particular at least 200° C., more in particular at least 230° C., or even at least 250° C. Preferably the temperature during this step does not exceed 400° C., in particular at most 350° C., more in particular at most 320° C.

The pressure during the process is not critical, as long as the reaction medium is in the liquid phase. As a general range, a value of 0.5 to 100 bar may be mentioned, depending on the desired temperature. It is preferred for the CO2 removal step to be carried out at a pressure of at least 5 bar, in particular at least 10 bar, to maintain a sufficient amount of amine and water in the medium. In view of the high costs associated with high-pressure apparatus, it may be preferred for the pressure to be at most 50 bar, in particular at most 40 bar.

The amount of water depends on the desired degree of conversion and on the process conditions. In general, the amount of water is at least 0.1 mole water per mole urea moiety in the feedstock. Higher amounts are often used, e.g., at least 0.2 mole water per mole urea moiety, in particular at least 0.5 mole water per mole urea moiety. The maximum is not critical for the process according to the invention but too large amounts of water will lead to unnecessarily large equipment being required. As a general maximum an amount of at most 500 mole water per mole cyclic alkyleneurea moiety may be mentioned, in particular at most 300 mole, more in particular at most 200 mole, in some embodiments at most 100 mole, or at most 50 mole.

CO2 removal can be carried out when the conversion of the alkyleneureas into ethyleneamine compounds using water has been completed. However, it is preferred to carry out CO2 removal during the conversion reaction. CO2 removal can be carried out in manners known in the art. The most basic way to do this it to vent the reaction vessel.

A stripping gas can be used to increase CO2 removal. Other measures to improve removal of CO2 will be evident to the skilled person, and include measures to increase mass transfer between the liquid phase and the gas/vapour phase, and include measures like stirring of the reaction mixture, sparging of stripping gas, thin-film evaporation, use of packing or trays, etc.

Where a stripping gas is used, the flow rate is typically at least 1 m3 per 1 m3 reactor volume per hour (at reaction temperature and pressure), and at most 100 m3 per 1 m3 reactor volume per hour (at reaction temperature and pressure). The stripping flow rate can be generated by evaporation of a liquid inside the reactor vessel, resulting in in situ generation of stripping gas. The ranges above also apply to this embodiment. Of course, it is also possible to combine the addition of tripping gas with the in situ formation of stripping gas.

The CO2-containing stripping fluid removed from the CO2 removal step can, for example, comprise from 1 to 99 mol. % CO2. In other embodiments, the stripping fluid may comprise 1-80 mol. % CO2, or 1-60 mol. % CO2. In some embodiments, the effluent from the CO2 removal step may comprise 1-40 mol. % CO2, or 1-20 mol. % CO2. Lower CO2 contents make for more efficient stripping, but also for the use of more stripping gas. It is within the scope of the skilled person to find an appropriate balance between these parameters.

Depending on the reaction temperature and the desired degree of CO2 removal, the reaction time can vary within wide ranges, e.g., at least one minute, in particular at least 5 minutes, more in particular between 15 minutes and 24 hours. In one embodiment, the reaction time may be at least 30 minutes, or at least 1 hour. It may be preferred for the reaction time to vary between 1 hour and 12 hours, in particular between 1 hour and 6 hours. When using lower temperatures, longer reaction times may be required to obtain the desired degree of conversion.

The conversion with water does not rely on the use of a strong inorganic base. Nevertheless, if so desired, a limited amount of strong inorganic base may be present. Within the context of the present invention, a strong inorganic base is a material which does not contain carbon-carbon bonds and which has a pKb of less than 1. In one embodiment, the strong inorganic base, if used, is selected from the group of metal hydroxides, in particular from the group of hydroxides of alkaline and earth alkaline metals, in particular from sodium hydroxide, potassium hydroxide, lithium hydroxide, calcium hydroxide, magnesium hydroxide, and barium hydroxide. In one embodiment, the strong inorganic base is selected from the group of metal oxides, in particular from the group of oxides of alkaline and earth alkaline metals, in particular from calcium oxide, magnesium oxide, and barium oxide. Selecting a strong inorganic base from the group of sodium hydroxide, potassium hydroxide, magnesium (hydr)oxide, and calcium (hydr)oxide may be preferred. The use of sodium hydroxide and potassium hydroxide may be particularly preferred. Other strong inorganic bases may also be used, such as ammonium hydroxide. As will be evident to the skilled person, mixtures of various strong inorganic bases can be used. Compounds comprising a strong base in addition to other components can also be used, as can be compounds which will be converted into strong inorganic bases in the reaction medium. If a strong inorganic base is used, it is generally used in an amount of less than 0.5 mole inorganic base per mole cyclic alkyleneurea moieties, in particular less than 0.2 mole inorganic base per mole cyclic alkyleneurea moieties.

In one embodiment of the present invention, the CO2 removal step is carried by reacting cyclic alkyleneureas in the liquid phase with water in an amount of 0.1-20 mole water per mole urea moiety, at a temperature of at least 230° C., with removal of CO2. It has been found that the use of a low amount of water in combination with a relatively high temperature and CO2 removal results in an efficient process which good conversion and low formation of side products.

It has been found that it is possible in this embodiment of the process according to the invention to obtain good conversion with the relatively limited amount of water of at most 20 mole water per mole urea moiety. It has been found that it possible to work at even lower amounts of water, e.g., and amount of at most 15 mole water per mole urea moiety, more in particular an amount of at most 10 mole water per mole urea moiety, or even at most 5 mole water per mole urea moiety.

The range of 0.1-20 mole water per mole urea moiety refers to the entire amount of water added during the process, calculated on the amount of urea moieties in feedstock at the start of the reaction. To obtain full conversion, 1 mole water is required per mole urea moiety to be converted. As full conversion is not always necessary, lower amounts of water may be possible. Therefore, water is used in an amount of at least 0.1 mole per mole urea moiety. Higher amounts are often used, e.g., at least 0.2 mole per mole urea moiety, in particular at least 0.5 mole water per mole urea moiety.

Water can be added at the beginning of the process in a single dosing. It is preferred, however, to add the water during the process, in several dosings or continuously. In a continuous operation multiple feedpoints may be used. By matching the amount of water added to the amount of water consumed by the reaction, the excess water in the reaction mixture can be limited. It has been found that this limits the formation of side products.

The molar ratio of water to urea moieties is calculated on the water present in the liquid reaction medium. If water is added in the form of steam, which may be an attractive embodiment to combine water addition with the provision of heat to the reaction mixture, the majority of water in the steam will not be absorbed in the liquid reaction medium. It is within the scope of the skilled person to regulate the conditions of a water addition process via steam in such a way that the desired amount of water is absorbed by the reaction medium. The water can also be present in the feedstock from the beginning of the reaction, e.g., as a result of the process by which the feedstock was produced. Water can also be added as a liquid.

In this embodiment of the present invention, the reaction is performed at a temperature of at least 230° C. It has been found that at a temperature below this value, the reaction rate is too low to obtain meaningful conversion in an acceptable time frame. It is preferred to carry out the reaction at a temperature of at least 240° C., in particular at least 250°. As a maximum value, a value of 400° C. may be mentioned. It may be preferred to carry out the reaction at a temperature of at most 350° C., in particular at most 320° C.

In this embodiment of the present invention the pressure is not critical, as long as the reaction medium is in the liquid phase. As a general range, a value of 0.5 to 100 bar may be mentioned. The preferred pressure ranges mentioned above also apply to this embodiment.

If so desired the CO2 removal step can be carried out with water in the presence of an amine compound selected from the group of primary amines, cyclic secondary amines, and bicyclic tertiary amines.

Primary amines are amine functional compounds in which the amine group is of the formula R4-NH2 and wherein R4 can be any organic group, preferably an aliphatic hydrocarbon with optional heteroatoms such as oxygen and/or nitrogen. Secondary cyclic amines are amines of the formula R5-NH—R6, wherein R5 and R6 together form a hydrocarbon ring, optionally with heteroatoms such as oxygen and/or nitrogen, preferably a piperazine ring. Tertiary bicyclic amines are amines of the formula R7-N(—R9)-R8 where R7 and R8 together form a hydrocarbon ring—optionally with heteroatoms such as oxygen and/or nitrogen—and R7 and R9 together form another hydrocarbon ring—optionally with heteroatoms such as oxygen and/or nitrogen.

On all the above groups R4 to R9 substituents can be present, like alkyl or hydroxyalkyl groups. Primary amines, cyclic secondary amine and bicyclic tertiary amines all contain a sterically relatively unhindered amine group. In this document a compound is defined as a primary amine or a secondary cyclic amine or a tertiary bicyclic amine if one of the amine groups in the compound is a primary amine or secondary cyclic amine or a tertiary bicyclic amine group, independent of if this compound contains further amine groups that may be different in their nature. A compound can also contain two or more different amine functionalities, e.g. a primary amine and a secondary cyclic amine functionality or a primary amine, a secondary cyclic amine and a tertiary bicyclic amine functionality.

Preferred examples of primary amines are alkylamines, linear ethyleneamines, and alkanolamines. Structures of some amine compounds are given in FIG. 1.

Preferred examples of cyclic secondary amines are amines that contain a terminal piperazine ring. Preferred examples of bicylic tertiary amines are 1,4-diazabicyclo [2.2.2]octane (DABCO), 1,4-diazabicyclo[2.2.2]octan-2-yl) methanol and 1-azabicyclo[2.2.2]octane (Quinuclidine).

The amine compound is preferably a compound with more than one amine group wherein at least one of the amine groups is a primary amine, even more preferably it is an amine wherein two amine groups are a primary amine. The amine compound is preferably a compound different than R1-NH-R3-NH—R2 that is obtained by the process of the invention.

In another preferred embodiment the amine compound is a compound that can bind with the carbonyl group from the cyclic ethyleneurea. Preferred amine compounds include an alkyleneamine, or an alkanolamine compound, even more preferably a smaller alkyleneamine, ethyleneamine, or alkanolamine, ethanolamine, than is formed by the process of the invention, most preferably ethylenediamine (EDA), diethylenetriamine (DETA), monoethanolaomine (MEA), aminoethylethanolamine (AEEA), N-aminoethylpiperazine (AEP), N, N'-diaminoethylpiperazine (DAEP), UDETA, N,N'-diaminoethyl-2-imidazolidinone (U2TETA), tris-aminoethylamine (TAEA).

In yet another preferred embodiment the amine compound is a compound that binds the carbonyl group from the cyclic alkyleneurea to give among others another linear or cyclic alkyleneurea or linear or cyclic alkylenecarbamate, that is larger or less volatile than the alkyleneamine formed by the process of the invention, even more preferably an ethyleneamine that is solid under the conditions used to work up the reaction mixture or an ethyleneamine bound to a solid carrier. Examples thereof are DETA-PS (i.e. a diethylene triamine linked to a solid polystyrene) or a solid polyethyleneimine (PEI).

Preferred amine compounds that can be used in the CO2 removal step of the process according to the invention include ethylenediamine (EDA), N-methylethylenediamine (MeEDA), diethylenetriamine (DETA), ethanolamine (MEA), aminoethylethanolamine (AEEA), piperazine (PIP), N-aminoethylpiperazine (AEP), 1,4-diazabicyclo[2.2.2]octane (DABCO), 1,4-diazabicyclo[2.2.2]octan-2-yl)methanol, triethylenetetramine (TETA), N-diethyldiamine-2-imidazolidinone (UITETA), N, N'-diaminoethylpiperazine (DAEP), N, N'-diaminoethyl-2-imidazolidinone (U2TETA), tetraethylenepentamine (TEPA), pentaethylenehexamine (PEHA), and the mono cyclic ureas of TEPA and PEHA (i.e. U1TEPA, U2TEPA, U1PEHA, U2PEHA, U3PEHA) and the dicyclic urea isomers of PEHA (i.e. DUPEHA), a polyethyleneimine (PEI) or an alkyleneamine on a solid carrier.

The amine compound is preferably dosed in a molar amount of between 0.001 and 100 equivalents in regard to the total molar amount of cyclic ethyleneurea, more preferably between 0.01 and 50 equivalents, even more preferably between 0.05 and 30 equivalents, yet more preferably between 0.15 and 25 equivalent and most preferably between 0.20 and 20 equivalents.

The reaction with water in the presence of an amine in the CO2 removal step is preferably carried out at a temperature of at least 150° C., preferably at least 200° C., more preferably at least 230° C., and most preferably of at least 240° C., or at least 250° C. Preferably the temperature during the process does not exceed 400° C., more preferably 350° C., even more preferable 320° C.

The reaction with water and amine compound in one embodiment of the first step of the process according to the invention is generally performed for a time of between 1 minute and 12 hours. Preferably the reaction is run in less than 10 hours, more preferably in less than 8 hours, most preferably less than 5 hours. Depending on the reaction temperature and the desired degree of CO2 removal, it may be preferred to for the reaction time to be at least 5 minutes, more in particular at least 15 minutes, at least 30 minutes, or at least 1 hour. When using lower temperatures, longer reaction times may be required to obtain the desired degree of conversion. As a skilled person will understand this reaction time does not include any further processing of the reaction mixture such as for separating the obtained compounds.

In a preferred embodiment, in the first step of the process according to the invention a cyclic ethyleneurea of TETA or TEPA, such as linear TETA diurea (DUTETA) or linear TEPA diurea (DUTEPA), is converted to linear TETA (L-TETA) or linear TEPA (L-TEPA) by employing an amine selected from the group of EDA, DETA, MEA, AEEA, N-methyl-EDA (MeEDA), AEP, DAEP, U2TETA, and TAEA. Particularly preferred are the amine compounds EDA, DETA, U2TETA, DAEP or AEP. The conversion of DUTETA with EDA and water proceeds preferably between 150 and 350° C., preferably between 200 and 300° C.

In the CO2 removal step, CO2 is removed from the system. The system comprises other volatile compounds such as water and in some embodiments low-boiling amines. The CO2 removal step focuses on the removal of CO2, and while evaporation of other volatiles may not be detrimental, it will generally be limited. This can, e.g., be done by the use of a condenser.

It is preferred for the composition provided to the CO2 removal step to consist for at least 70 wt. % of the total of water, cyclic alkylene ureas, in particular those indicated above as preferred, and if present, amine compounds selected from the group of primary amines, cyclic secondary amines, and bicyclic tertiary amines, in particular those indicated above as preferred. It is particularly preferred for the composition provided to the first step to consist for at least 80 wt. % of the total of these compounds, more in particular for at least 90 wt. %.

For reasons of process efficiency it is preferred for the amount of alkyleneamines removed from the system by evaporation during the CO2 removal step to be limited. In one embodiment, at least 80% of the total of alkyleneamines and cyclic alkyleneureas is retained in the system during the CO2 removal step, in particular at least 90%, more in particular at least 95%. As in the CO2 removal step cyclic alkyleneureas are converted into alkyleneamines, this percentage is to be calculated on the molecular total of cyclic alkyleneureas and alkyleneamines. It is preferred that the CO2 removal step is carried out without substantial removel of alkyleneamines from the system. This can be effected by selecting appropriate process conditions such as temperature, pressure, and whether or not a stripping agent is applied, and if so, the type of stripping agent. Further, suitable apparatus, e.g., a (partial) condenser section can be applied.

The Amine Removal Step

In the amine removal step cyclic alkyleneureas are converted in a reactive separation process into their corresponding alkyleneamines by reaction with an amine compound selected from the group of primary amines or secondary amines which have a higher boiling point than the alkyleneamines formed during the process.

The crux of the alkyleneurea removal step is that alkyleneureas are reacted with an amine compound selected from the group of primary amines or secondary amines which have a higher boiling point than the alkyleneamines formed during the process. In this process alkyleneureas are converted to alkyleneamine compounds which are removed from the system and amine compounds selected from the group of primary amines or secondary amines which have a higher boiling point than the alkyleneamines formed during the process are converted to alkyleneureas or alkylenecarbamates, which remain in the system.

This step makes it possible to form the alkyleneamine product with high efficiency and simultaneously separate it from the reaction mixture in a good yield using relatively mild conditions. The alkyleneneamines formed can be prepared and isolated as one fraction at relatively low temperatures, especially relatively volatile alkyleneneamines. Because amines are used to convert cyclic alkyleneureas into their corresponding alkyleneamines, degradation of the alkyleneamines is avoided to a large extent. The process of the present invention has as a further advantage that water or any other adjuvant need not be added and that the alkyleneureas and alkylenecarbamates formed in the process can be also recovered as products.

Examples of reactive separation processes are process driven by volatility differences such as for example reactive flashing, membrane distillation, membrane evaporation stripping or reactive distillation, wherein reactive distillation is preferred.

The amine removal step can for many embodiments be represented by the following reaction: UEA1+EA2→EA1 ↑+UEA2 wherein UEA1 is the cyclic alkyleneurea, EA2 the amine compound, and the up-arrow indicates that the formed alkyleneamine EA1 is separated from the reaction mixture, and wherein EA2 has a higher boiling point than EA1.

The reaction mixture provided to the amine removal step may or may not contain water. If substantial amounts of water are present in this mixture it may be preferred to first remove water from the system. Therefore, in one embodiment, a water removal step is carried out before the amine removal step. Such a step may involve a water evaporation, flashing, stripping, extraction, adsorption or other physical step as well as chemical water scavenging techniques known to the person skilled in the art, preferably by a distillation step.

It is preferred for the water content of the reaction mixture provided to the amine removal step to be less than 10 wt. %. In a preferred embodiment of the process the reaction mixture contains less than 7 wt. %, even more preferred less than 5 wt. % of water on the basis of total weight of the reaction mixture.

In one embodiment of the present invention, the water concentration of the material subjected to the $CO_2$ removal step is higher than the water concentration of the material subjected to the amine removal step. To ensure this, it may be necessary to effect a water removal step between the $CO_2$ removal step and the amine removal step.

The amine removal step may be conducted at any suitable pressure. During the reaction, the pressure in the reactive separation system preferably is at most 127 bara, more preferably at most 50 bara, and even more preferably at most 25 bara. The larger the alkyleneamine produced is, the more preferable an even lower pressure is. For example, if the alkyleneurea to be converted is a urea derivative of diethylenetriamine, the pressure preferably is less than 15 bar. If the alkyleneurea to be converted is a urea derivative of triethylenetetramine, the pressure preferably is less than 5 bar. Hence, in some embodiments of the process according to the invention the process is performed at even lower pressures, such as less than 15 bar or even more preferably lower pressure, such as less than 5 bar.

The process can also be carried out at a pressure below atmospheric pressure, such as less than 700 mbara, more preferably below 100 mbara, even more preferably below 25 mbara, and most preferably below 5 mbara.

In general the pressure will be at least 0.1 mbara.

The pressure in the amine removal step is generally lower than the pressure in the $CO_2$ removal step.

The amine removal step is preferably carried out at a temperature of at least 150° C., in particular at least 180° C., in some embodiments at least 200° C., or at least 230° C., sometimes at least 250° C. Preferably the temperature during the process does not exceed 400° C., more preferably 350° C.

In one embodiment, the amine removal step is carried out at a temperature in the range of 180–300° C. and a pressure of at most 2000 mbara, in particular at most 1000 mbara, more in particular at most 500 mbara, more in particular at most 200 mbara. It may be preferred to carry out the amine removal step at a temperature of 200-260° C. and a pressure of at most 50 mbara.

The amine removal step generally is performed for a time of between 1 minute and 12 hours. Preferably the amine removal step is run in less than 10 hours, more preferably in less than 8 hours, most preferably less than 5 hours.

The crux of the amine removal step is that alkyleneureas are reacted with an amine compound selected from the group of primary amines or secondary amines which have a higher boiling point than the alkyleneamines formed during the process.

The amine compound can be a primary amine or secondary amine. Primary amines are amine functional compounds in which the amine group is of the formula R4-NH2 and wherein R4 can be any organic group, preferably an aliphatic hydrocarbon with optional heteroatoms such as oxygen and/or nitrogen. Secondary amines are amines of the formula R5-NH—R6, wherein R5 and R6 can be any organic group, preferably an aliphatic hydrocarbon with optional heteroatoms such as oxygen and/or nitrogen. Secondary amines can be either linear or cyclic. On all the above groups R4 to R6 substituents can be present, like alkyl, aminoalkyl, or hydroxyalkyl groups.

In this document a compound is defined as a primary amine or a secondary amine if one of the amine groups in the compound is a primary amine or secondary amine, independent of if this compound contains further amine groups that may be different in their nature. A compound can also contain two or more different amine functionalities, e.g. a primary amine and a secondary amine functionality, and can also contain more than one of each.

Preferred examples of primary amines are alkylamines, linear alkyleneamines, and alkanolamines.

The amine compound is preferably a compound with more than one amine group wherein at least one of the amine groups is a primary amine, even more preferably it is an amine wherein two amine groups are a primary amine, or wherein one amine is a primary amine group and that in addition contains a hydroxyl group. The amine compound is preferably a compound different than R1-NH-R3-NH—R2 that is obtained by the process of the invention.

In another preferred embodiment the amine compound is a compound that can bind with the carbonyl group from the cyclic alkylene urea (UEA). Preferred amine compounds include an alkylene amine, optionally containing a piperazine unit in their structure, or an alkanol amine compound, optionally containing a piperazine unit in their structure, even more preferably an amine compound that binds the carbonyl group from the cyclic alkylene urea to give among others another linear or cyclic alkylene urea or linear or cyclic alkylene carbamate, that is larger or less volatile than the alkylene amine formed by the process of the invention. Alkylene amines, possibly partially converted into their cyclic alkylene urea counterparts are preferred over alkanolamines (and over alkanolamine counterparts wherein a conversion to a carbamate or urea of these alkanolamines found place).

The amine compounds that are preferably used are in embodiments ethylenediamine (EDA), N-methylethylenediamine (MeEDA), diethylenetriamine (DETA), ethanolamine (MEA), aminoethylethanolamine (AEEA), HE-DETA, HE-TETA, HE-UTETA, linear triethylenetetramine (L-TETA), N-diethyldiamine-2-imidazolidinone (U1TETA), N, N'-diaminoethyl-2-imidazolidinone (U2TETA), linear tetraethylenepentamine (L-TEPA), pentaethylenehexamine (PEHA), and the mono cyclic ureas of TEPA and PEHA (i.e. U1TEPA, U2TEPA, U1PEHA, U2PEHA, U3PEHA), the dicyclic urea isomers of PEHA (i.e. DUPEHA), and the C1, C2, C3 analogues of the alkylene amines such as C1TETA (N1-(2-(piperazin-1-yl)ethyl)ethane-1,2-diamine), C1TEPA (N1-(2-aminoethyl)-N2-(2-(piperazin-1-yl)ethyl)ethane-1, 2-diamine), C2TEPA (N1-(2-(4-(2-aminoethyl)piperazin-1-yl)ethyl)ethane-1,2-diamine), C1PEHA (N1-(2-aminoethyl)-N2-(2-((2-(piperazin-1-yl)ethyl)amino)ethyl)ethane-1,2-diamine), C2PEHA (N1-(2-aminoethyl)-N2-(2-(4-(2-aminoethyl)piperazin-1-yl)ethyl)ethane-1,2-diamine) and C3-PEHA (N1,N1'-(piperazine-1,4-diylbis(ethane-2,1-diyl)) bis(ethane-1,2-diamine).

More preferred combinations of cyclic alkylene ureas and amine compounds are in below Table 1

TABLE 1

| Cyclic alkylene urea | The amine compound |
| --- | --- |
| EU | DETA, TETA, TEPA, PEHA, AEEA, HE-DETA, HE-TETA, UTETA, UTEPA, UPEHA, HE-UTETA, |
| UDETA | TETA, TEPA, PEHA, AEEA, HE-DETA, HE-TETA, UTETA, UTEPA, UPEHA, HE-UTETA |
| UAEEA | TETA, TEPA, PEHA, HE-DETA, HE-TETA, UTETA, UTEPA, UPEHA, HE-UTETA, |
| UTETA, or DUTETA | TEPA, PEHA, HE-DETA, HE-TETA, UTETA, UTEPA, UPEHA, or HE-UTETA |
| HE-UDETA | TEPA, PEHA, HE-TETA, UTEPA, UPEHA, or HE-UTETA |
| UTEPA or DUTEPA | PEHA, HE-TETA, UTEPA, UPEHA, or HE-UTETA |
| UPEHA, DUPEHA or TUPEHA | UPEHA, or HE-UTETA |

For some of the above molecules the position of the U is not mentioned, as it can be at any place at the molecule, i.e., UTETA can be U1TETA or U2TETA It should be understood that the process of the invention can also be employed for reaction mixtures that contain two or more amine compounds and/or cyclic urea compounds.

In one embodiment, the amine compound is present during the process in a molar amount of between 0.15 and 25 equivalent based on the total molar amount of cyclic alkyleneurea.

The amine used as reactant in the amine removal step may be the same or different as the amine that may be present in the CO2 removal step described above.

It is possible to carry out the amine removal step in a single step. However, if the starting materials contains a number of different components with varying boiling ranges, it may be attractive to carry out the amine removal step in at least two stages, wherein the boiling point of the alkyleneamines removed increases with the stage. That is, the alkyleneamines removed in the first stage have a boiling point which is below that of at least some of the alkyleneamines removed in the second stage, which in turn is lower than the boiling point of the alkyleneureas removed in the third stage, if present, and so on.

For example, in a first step, EU may react with a higher boiling amine compound to form EDA, which is removed by distillation, and a cyclic alkylene urea, and in a second step, UDETA may react with a higher-boiling amine compound to form DETA, which can be removed by distillation, and a cyclic alkylene urea.

If so desired, CO2 may also be removed during the amine removal step. Especially continuous removal will enhance the process. The carbon dioxide can be removed for example by working in a suitable reactor unit comprising or connected to a section for actively removing CO2 by desorption, for instance by distillation, stripping or flashing, with or without a membrane.

The amine separation step can be carried out in a batch reactor, possibly fed-batch operation, or in a continuously operating system such as in a cascade of continuous flow reactor. Someone skilled in the art will be able to select the right reactor setup. The same applies to the CO2 removal step.

In the large-scale production of chemicals it is preferred to employ a continuous process. The continuous process may be, for example, a single-pass or a recycle process. In a single-pass process, one or more of the reagents pass through the process equipment once, and then the resulting effluent from the reactor is sent for purification or further processing.

In such a scheme, the cyclic alkyleneurea, amine compound and possibly water may be fed to the equipment as desired at a single point or at multiple points throughout the process equipment, which may include continuously stirred tank reactors, tubes, pipes, reactive distillation columns, reactive stripping units or combinations thereof.

In embodiments wherein a reactive distillation apparatus is used, the apparatus may comprise a reactive distillation column comprising at least one column internal (separation stage), which column is on one side connected to a cooler unit and on the other side connected to a reboiler, and which apparatus is provided with an inlet for supplying the amine mixture, and one or more outlets for different distillate fractions. The process can be operated in batch-mode or continuously.

The process of the present invention typically depends on a number of reaction parameters such as the pressure in the column, the mass ratio of H2O to amine, the CO over amine fraction, the number and/or type of trays of the reactive distillation column, the temperature of the cooler unit and/or reboiler, and the liquid residence time in the said column.

The reactive distillation column comprises at least one column internal. Examples of such a column internal are a tray or packing. The number of trays of the reactive distillation column is also an important reaction parameter as these determine the effectiveness of the separation process of the reactants and products that takes place in the column, simultaneously with the reactions. Preferably, the number of trays in the column is at least 1, more preferably at least 2, and most preferably at least 5, and preferably at most 80, more preferably at most 60, most preferably at most 40. A skilled person further would understand that the size of the trays and the volume of the liquid, which each tray can contain, can vary and will also influence the reaction and/or separation effectiveness.

Desirably, the column will have trays, but any gas liquid contacting device might be suitable. Alternatively, suitable conventional packing, such as Raschig rings, Pall rings, saddles or structured packing of any kind might be used instead of trays. The different sections in the column might be equipped with different types of packing and/or trays.

The temperature of the cooler unit is lower than the reboiler temperature, and is chosen such that low-boiling products, such as the ethyleneamine compound formed can leave the column, and that the reactants and high-boiling products remain in the system. The cooler unit can comprise just one cooler unit or may comprise a plurality of cooler sub-units, whereby each sub-unit has a specific temperature. A preferred embodiment of such a cooler unit comprises a first and a second cooler sub-unit. In a preferred embodiment a cooler unit is a condenser.

The person skilled in the art is capable of selecting the proper reactor and separation unit scheme by determining the overall yield, energy consumption and waste production.

In a most preferred embodiment a cyclic alkyleneurea of EDA, DETA, TETA or TEPA, such as EU, UDETA, linear TETA mono- or diurea (UTETA or DUTETA) or linear TEPA mono or diurea (UTEPA or DUTEPA), is converted to EDA, DETA, linear TETA (L-TETA) or linear TEPA (L-TEPA) by employing EDA, DETA, TETA, TEPA, or larger ethyleneamines. Cyclic alkyleneureas of AEEA can advantageously be converted to AEEA with the process according to the invention.

As will be evident to the skilled person various embodiments of the present invention, and various preferences expressed herein can be combined as long as they are not mutually exclusive.

Figure 2:
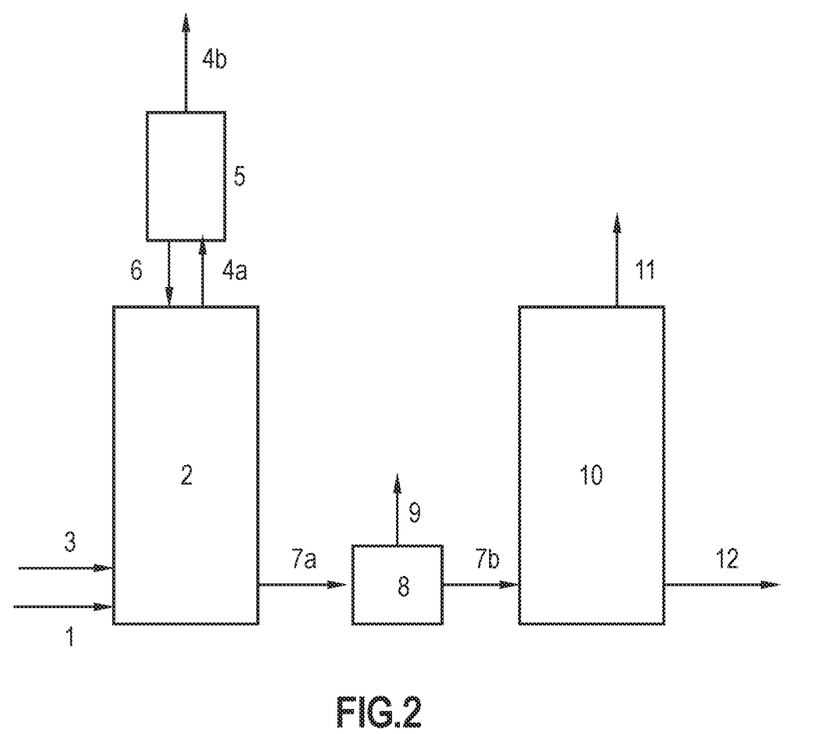
FIG. 2 illustrates one embodiment of the process according to the invention.

FIG. 2 illustrates one embodiment of the process according to the invention.

A feed containing cyclic alkylene ureas is provided through line (1) to a CO2 removal unit (2). In the CO2 removal unit, water is provided through line (3). A stripping gas can be provided through lines not shown. The mixture is brought to CO2 removal conditions as discussed above. CO2 is removed through line (4a). If so desired, line (4a) can pass through a condenser where evaporated amine is condensed and fed back to CO2 removal unit (2) through line (6), with the CO2 being removed through line (4b).

The product of the CO2 removal step is a mixture of ethyleneamines and cyclic alkyleneureas, which is withdrawn through line (7a). If so desired, it can be provided to an intermediate separation step (8), where light fractions, in particular water are removed through line (9). The product from which light fractions have optionally been removed is provided through line (7b) to an amine removal step in unit (10), where a reactive separation step takes place. In unit (10), the mixture is brought to amine removal conditions as discussed above. Cyclic alkyleneureas are converted (by reaction with an amine) to the corresponding alkyleneneamines, which are removed through line (11). Simultaneously, higher-boiling alkyleneureas are formed, which remain in the reaction unit, and can be removed through line (12). The product of the reactive separation step thus has a higher CO2 loading than the feed provided to the reactive separation step. As described elsewhere, it is possible to provide the product of the amine removal step, as a whole or in part, and optionally after having been combined with other fractions to a further CO2 removal step (not shown).

In the figures, the steps are described as being carried out separate units. However, as will be evident to the skilled person, it is also possible to carry out the process in a single unit in sequential steps.

The invention will be elucidated by the following examples, without being limited thereto or thereby.

Comparative Example 1: $CO_2$ Removal Step Only

A feed comprising 0.64 mol (93.6 g) of L TETA and 0.63 mol (124.5 g) DUTETA was provided to a reaction vessel. The reaction vessel was equipped with a stirrer and a gas sparger connected to a nitrogen gas bottle, and connected to a syringe pump filled with water. The reactor was operated at a pressure of 35 bara using a pressure control valve and a liquid temperature of 265° C. in the reactor vessel. Water was dosed during the process to compensate for water evaporated during the CO2 removal step. The nitrogen gas flow rate was controlled using a mass flow controller at a flow rate of 1 L/min. The stirrer was operated at 2500 rpm. The CO2 removal step was started by starting the provision of the stripping gas once operating temperature was reached. The reaction was carried out for 330 minutes. The amount of CO2 removed during the reaction was monitored using a near-infrared CO2 gas analyser. One the reaction has been stopped, the mixture was cooled down and the reaction product was analysed using a GC-FID (gas chromatography using a flame ionization detector). The compositions of the starting material and the reaction product are provided in Table 1.

TABLE 1

| Component | Dosed at start | After CO2 removal |
| --- | --- | --- |
| L-TETA (mol) | 0.64 | 0.45 |
| DUTETA (mol) | 0.63 | 0.034 |
| U1TETA (mol) | 0 | 0.25 |
| U2TETA (mol) | | 0.28 |
| U total (mol) | 1.3 | 0.63 |
| Amine total (mol) | 1.3 | 1.2* |
| CO2 removed from liquid (mol) | N/A | 0.672 |
| Average CO2 removal rate (mmol/min) | | 2.28 |
| CO2 loading | 0.5 | 0.29 |

*some amine was lost due to evaporation.

From Table 1 it can be seen that the CO2 removal step as carried out herein results in a decrease in CO2 loading of 0.5 to 0.29.

Example 2 According to the Invention: Amine Removal Followed by CO2 Removal

In this example, the feedstock of Comparative example 1 is subjected to a reactive separation step to effect amine removal, followed by a CO2 removal step.

The amine removal step was carried out as follows: 0.64 mol (93.6 g) of L-TETA and 0.63 mol (124.5 g) DUTETA were provided to a stirred reaction vessel. The vessel was heated to a starting temperature of 200° C., and brought to a pressure of 20 mbara using a vacuum pump. This pressure was maintained during the process. The temperature was slowly increased during the reaction to an end value of 260° C. The reaction was stopped after 33 minutes.

The vapour collected from the reactor, that is, the ethylene amine, was cooled down using a cold trap containing ice that was placed between the cooler and the vacuum pump. The evaporated product and the product remaining in the reactor were analysed using a GC-FID.

The product remaining in the reactor was subjected to a CO2 removal step as described in Example 1. The reaction was stopped after 260 minutes. Table 2 shows the composition of the starting material, the gas fraction after the reactive separation step, the liquid fraction after the reactive separation step, the product from the CO2 removal step, and the total of the gas fraction from the amine removal step and the CO2 removal step.

TABLE 1

| Component | Dosed at start | gas fraction from amine removal step | liquid fraction from amine removal step | product from $CO_2$ removal step | total result from process |
|---|---|---|---|---|---|
| L-TETA (mol) | 0.64 | 0.56 | 0.04 | 0.11 | 0.67 |
| DUTETA (mol) | 0.63 | | 0.59 | 0.05 | 0.05 |
| U1TETA (mol) | | | 0.08 | 0.16 | 0.16 |
| U2TETA (mol) | | | | 0.11 | 0.11 |
| U total (mol) | 1.27 | | 1.27 | 0.40 | 0.40 |
| Amine total (mol) | 1.27 | | 0.71 | 0.48 | 1.04 |
| U removed from liquid (mol) | | | | 0.87 | |
| Average CO2 removal rate (mmol/min) | | | | 3.35 | |
| CO2 loading | 0.5 | | 0.89 | 0.45 | 0.20 |

Table 3 below shows the results of comparative example 1 and example 2 according to the invention side by side.

TABLE 2

Main number comparison of the examples

| | Example 1 Comparative CO2 removal alone | Example 2 invention Amine removal followed by CO2 removal |
|---|---|---|
| Reaction time needed (min) | 330 | 293 |
| U2TETA byproduct (mol) | 0.28 | 0.11 |
| Total L-TETA recovered (mol) | 0.45 | 0.67 |
| Average removal rate (mmol/min) | 2.28 | 3.35 |
| CO2 loading at start | 0.5 | 0.5 |
| CO2 loading after reactive distillation | | 0.89 |
| CO2 loading at end | 0.29 | 0.2 |

As can be seen from table 3, the process according to the invention yields more L-TETA than the comparative process. The formation of the undesired U2TETA byproduct is reduced. The time required to effect CO2 removal is reduced. The CO2 loading of the end product is also reduced.

Comparative Example 3: CO2 Removal Only

Example 1 was repeated, except that a starting material was used comprising 0.27 mol (38.9 g) of L TETA, 0.78 mol (154.9 g) DUTETA and 2.29 mol (41.3 g) water. The starting material had a CO2 loading of 0.75. A reaction time of 290 minutes was employed.
Table 4 provides the composition of the starting material and the product.

TABLE 4

| Component | Dosed at start mol | After reactive stripping mol |
|---|---|---|
| L-TETA (mol) | 0.27 | 0.32 |
| DUTETA (mol) | 0.78 | 0.074 |
| U1TETA (mol) | | 0.307 |
| U2TETA (mol) | | 0.276 |
| U total (mol) | 1.56 | 0.76 |
| Amine total (mol) | 1.05 | 0.96* |
| U removed from liquid (mol) | N/A | 0.87 |
| Reaction time (mm) | | 290 |
| Average U removal rate (mmol/min) | | 2.98 |
| CO2 loading | 0.75 | 0.40 |

*Some amine was lost during evaporation

From this table it can be seen that the CO2 loading of the mixture is reduced from 0.75 to 0.4, at a reaction rate of 2.98 mmol/min. The reaction mainly results in the formation of the mono-urea compounds U1TETA and U2TETA from the diurea compound DUTETA.

Example 4 According to the Invention: CO2 Removal, Followed by Amine Removal, Followed by CO2 Removal The starting material used in Example 3 was subjected to a CO2 removal step as described in Example 3, except that the reaction was carried out for 93 minutes.

The liquid product from the CO2 removal step was subjected to an amine removal step as described in Example 2. A total of 0.27 mol (39.5 g) of L-TETA was removed during the reactive distillation step.

The liquid residue from the amine removal step was subjected to a further CO2 removal step, for 100 minutes. Table 5 below shows

| | Dosed at start | gas fraction amine removal step | liquid product after first $CO_2$ removal step, amine removal step, and second $CO_2$ removal step 2 | total result from process |
|---|---|---|---|---|
| L-TETA (mol) | 0.27 | 0.27 | 0.20 | 0.47 |
| DUTETA (mol) | 0.78 | | 0.11 | 0.11 |
| U1TETA (mol) | | | 0.33 | 0.33 |
| U2TETA (mol) | | | 0.19 | 0.19 |
| U total (mol) | 1.56 | | 0.77 | 0.77 |
| Amine total (mol) | 1.1 | | 0.83 | 1.1 |
| U removed from liquid (mol) | | | 0.79 | |
| Reaction time (mm) | | | 193 min | |
| Average U removal rate Based on GC data (mmol/min) | | | 4.11 | |
| CO2 loading | 0.75 | | 0.45 | 0.31 |

Conclusion

Table 3 shows the comparison of a number of process efficiency parameters for the example 3 and example 4. For all parameters, the performance of example 4 using a combination of the $CO_2$ removal step, the amine removal step, and another $CO_2$ removal step was better and the $CO_2$ removal step alone. In the case of reactive distillation combined with reactive stripping, the yield of L-TETA was higher, at a lower amount of added water was required. The average removal rate of CO2 was 38% higher in example 4 with respect to example 3. This example clearly shows the beneficial effect of performing the reactive distillation step in between two the reactive stripping steps.

TABLE 3

Main number comparison of the examples

|  | Example 3 comparative Reactive stripping alone | Example 4 invention Reactive stripping + Reactive distillation + reactive stripping |
|---|---|---|
| Reaction time needed (min) | 290 | 193 |
| U2TETA byproduct (mol) | 0.276 | 0.20 |
| Total L-TETA recovered (mol) | 0.32 | 0.47 |
| Average removal rate (mmol/min) | 2.98 | 4.11 |
| CO2 loading @ start | 0.75 | 0.75 |
| CO2 loading @ end (according to patent definition) | 0.40 | 0.31 |

Thus, the process according to the invention makes it possible to recover more L-TETA with reduced formation of U2TETA. Additionally, the time required to effect CO2 removal can be reduced.

Example 5 According to the Invention: Amine Removal Followed by CO2 Removal

In this example, a feedstock as described in Table 7 (starting mixture) is subjected to a reactive separation step to effect amine removal, followed by a CO2 removal step. The starting mixture was prepared by heating EDA (200 g, 3.32 mol), EU (128 g, 1.42 mol) and UAEEA (260 g, 1.90 mol) in a 2 L pressure autoclave at 290° C. for 80 min. The mixture was allowed to cool and was analyzed by GC-FID.

The amine removal step was carried out as follows: the mixture was heated at temperatures above 120° C. under reduced pressure (30-40 mbar) for 30 minutes and the volatiles were collected in a cold trap (130 g, ca 16 g water, ca 114 g EDA).

The product remaining in the reactor was subjected to a CO2 removal step, carried out as follows: 180 g water was added to the remaining mixture (429 g) at ambient temperature. The mixture was heated, the pressure was set to 30 barg and a flow of nitrogen (3 NL/min on average) was introduced via a micron sparger at the bottom of the vessel (equipped with a condenser set at 15° C. and a pressure regulator on top of the condenser) when the temperature reached 220° C. (t=0 min). The temperature slowly increased from 250° C. to the setpoint of 290° C. The reactor was allowed to cool after 190 minutes. A sample was analyzed by GC-FID and the remaining weight was 386 g.

|  | Starting mixture Mass % | After amine removal Mass % | After CO2 removal |
|---|---|---|---|
| EDA (wt %) | 20.8% | 2.3% | 12.3% |
| AEEA (wt %) | 2.9% | 3.7% | 6.6% |
| EU (wt %) | 17.2% | 23.8% | 2.0% |
| L-TETA (wt %) | 0.5% | 0.6% | 5.9% |
| E2U (wt %) | 3.0% | 3.7% | 0.0% |
| UAEEA (wt %) | 16.9% | 23.3% | 7.4% |
| U2-TETA (wt %) | 2.0% | 2.7% | 10.4% |
| U1-TETA (wt %) | 5.1% | 6.9% | 12.7% |

-continued

|  | Starting mixture Mass % | After amine removal Mass % | After CO2 removal |
|---|---|---|---|
| DUTETA (wt %) | 9.5% | 13.0% | 5.5% |
| U total (mol) | 2.9 | 2.9 | 1.08 |
| Amine total (mol) | 4.82 | 2.97 | 2.16 |
| Amine moieties available (mol) | 5.45 | 3.61 | 2.94 |
| U loading | 0.53 | 0.81 | 0.37 |
| Reaction time needed (min) |  |  | 190 |
| U2TETA byproduct (mol) |  |  | 0.23 |
| Total L-TETA recovered (mol) |  |  | 0.16 |
| Average removal rate (mmol/min) |  |  | 9.5 |
| CO2 loading @start |  |  | 0.53 |
| CO2 loading @end (according to patent definition) |  |  | 0.37 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A process for converting a feedstock comprising cyclic alkyleneureas into their corresponding alkyleneamines, comprising:
a $CO_2$ removal step in which cyclic alkyleneureas are converted into their corresponding alkyleneamines by reacting cyclic alkyleneureas in the liquid phase with water with removal of $CO_2$, and
an amine removal step wherein cyclic alkyleneureas are converted in a reactive separation process into their corresponding alkyleneamines by reaction with an amine compound selected from the group of primary amines or secondary amines which have a higher boiling point than the alkyleneamines formed during the process, wherein the cyclic alkyleneurea that is subjected to the conversion to give a corresponding alkyleneamine are:

wherein $R_1$ is chosen from the group of hydrogen, an alkyleneamine group of the formula $X-R_3-(NH-R_3-)_p-$, an alkoxy group of formula $X-R_3-(O-R_3-)_n-$, or a group combining such alkyleneamine and alkoxy units p and n, wherein one or more units $\sim N-R_3-N\sim$ in the alkyleneamine is present as and/or wherein one or more units —N—R$_3$—N— in the corresponding cyclic alkyleneurea is present as wherein R$_2$ is hydrogen, X is hydroxyl, amine, a linear or branched C1-C20 hydroxyalkyl or C1-C20 aminoalkyl group, optionally containing one or more piperazine or alkyleneurea groups, when n and p independently are at least 1, or when p or n is 0 is a C1-C20 hydroxyalkyl or C1-C20 aminoalkyl, and wherein each R$_3$ independently is alkylene or substituted alkylene.

2. The process according to claim 1 wherein in the CO$_2$ removal step from about 5% to about 95% of alkyleneurea moieties present in the feedstock are converted into amine moieties, and in the amine removal step from about 5% to about 95% of alkyleneurea moieties present in the feedstock are converted into amine moieties.

3. The process of claim 1 wherein the feed to the CO$_2$ removal step has a CO$_2$-loading of from about 0.2 to about 1.

4. The process of claim 1 wherein the feed to the amine removal step has a CO$_2$-loading of from about 0.05 to about 0.8.

5. The process of claim 1 comprising the steps of:
providing a feedstock with a CO$_2$-loading of at least about 0.2 to a CO$_2$ removal step in which cyclic alkyleneureas are converted into their corresponding alkyleneamines by reacting cyclic alkyleneureas in the liquid phase with water with removal of CO$_2$, and
providing at least part of the product of the CO$_2$ removal step to an amine removal step wherein cyclic alkyleneureas are converted in a reactive separation process into their corresponding alkyleneamines by reaction with an amine compound selected from the group of primary amines or secondary amines which have a higher boiling point than the alkyleneamines formed during the process.

6. The process of claim 1 further comprising the steps of:
providing a feedstock with a CO$_2$-loading of from about 0.05 to about 0.8 to an amine removal step wherein cyclic alkyleneureas are converted in a reactive separation process into their corresponding alkyleneamines by reaction with an amine compound selected from the group of primary amines or secondary amines which have a higher boiling point than the alkyleneamines formed during the process, and
providing at least part of the product of the amine removal step to a CO$_2$ removal step in which cyclic alkyleneureas are converted into their corresponding alkyleneamines by reacting cyclic alkyleneureas in the liquid phase with water.

7. The process of claim 1 wherein the CO$_2$ removal step is carried out at a temperature of from about 150° C. to about 400° C.

8. The process of claim 1 wherein the CO$_2$ removal step is carried by reacting cyclic alkyleneureas in the liquid phase with water in an amount of from about 0.1 to about 20 mole water per mole urea moiety, at a temperature of at least about 230° C.

9. The process of claim 1 wherein the CO$_2$ conversion step is carried out in the presence of an amine compound selected from the group of primary amines, cyclic secondary amines, and bicyclic tertiary amines.

10. The process of claim 1 wherein the amine removal step is a reactive distillation step.

11. The process of claim 1 wherein the water content of the feed to the amine separation step is less than about 10 wt. %.

12. The process of claim 1 wherein the pressure in the reactive separation system is at most about 127 bara.

13. The process of claim 1 wherein the amine removal step is carried out at a temperature of from about 150° C. to about 400° C.

14. The process of claim 1 wherein the feed to the CO$_2$ removal step has a CO$_2$-loading of from about 0.6 to about 1.

15. The process of claim 1 wherein the feed to the amine removal step has a CO$_2$-loading of from about 0.2 to about 0.6.

16. The process of claim 1 wherein the CO$_2$ removal step is carried out at a temperature of from about 250° C. to about 320° C.

17. The process of claim 1 wherein the amine removal step is carried out at a temperature of from about 250° C. to about 320° C.

* * * * *